(12) United States Patent
Kadowaki et al.

(10) Patent No.: US 8,895,011 B2
(45) Date of Patent: *Nov. 25, 2014

(54) INSULIN-RESISTANCE-IMPROVING DRUG

(75) Inventors: Takashi Kadowaki, Tokyo (JP);
Kohjiro Ueki, Tokyo (JP); Yukiko Okazaki, Tokyo (JP); Matthias Bluher, Leipzig (DE); Sumiko Ozawa, Tokyo (JP)

(73) Assignees: The University of Tokyo, Tokyo (JP); Sekisui Medical Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/699,876

(22) PCT Filed: May 27, 2011

(86) PCT No.: PCT/JP2011/062296
§ 371 (c)(1),
(2), (4) Date: Mar. 4, 2013

(87) PCT Pub. No.: WO2011/149096
PCT Pub. Date: Dec. 1, 2011

(65) Prior Publication Data
US 2013/0156793 A1    Jun. 20, 2013

(30) Foreign Application Priority Data

May 27, 2010  (JP) ................. 2010-122037
May 27, 2010  (JP) ................. 2010-122150

(51) Int. Cl.
| | |
|---|---|
| *A61K 39/395* | (2006.01) |
| *C07K 16/18* | (2006.01) |
| *C12N 15/113* | (2010.01) |
| *G01N 33/50* | (2006.01) |
| *A61K 31/7125* | (2006.01) |
| *G01N 33/68* | (2006.01) |
| *A61K 31/00* | (2006.01) |
| *C12Q 1/68* | (2006.01) |
| *A61K 38/22* | (2006.01) |
| *A61K 39/00* | (2006.01) |

(52) U.S. Cl.
CPC ............ *A61K 39/3955* (2013.01); *C07K 16/18* (2013.01); *C12N 15/113* (2013.01); *G01N 33/5008* (2013.01); *A61K 31/7125* (2013.01); *G01N 33/6893* (2013.01); *A61K 31/00* (2013.01); *C07K 2317/76* (2013.01); *C12Q 1/686* (2013.01); *A61K 2039/505* (2013.01); *C12N 2310/14* (2013.01); *A61K 38/22* (2013.01)
USPC .................. 424/172.1; 435/6.12; 435/7.1

(58) Field of Classification Search
None
See application file for complete search history.

(56) References Cited

U.S. PATENT DOCUMENTS

| | | | |
|---|---|---|---|
| 7,192,717 B2 * | 3/2007 | Hill et al. ............. | 435/7.1 |
| 2006/0281174 A1 * | 12/2006 | Xu et al. ............. | 435/325 |

FOREIGN PATENT DOCUMENTS

| | | |
|---|---|---|
| JP | 10-298100 A | 11/1996 |
| WO | WO 03/063594 A1 | 8/2003 |

OTHER PUBLICATIONS

Razanajaona et al (Cancer Res 2007; 67:7223-7229).*
Ma (Modern Drug Discovery 2004, 7(6)).*
International Search Report issued Aug. 16, 2011, in PCT International Application No. PCT/JP2011/062296.
Mukherjee et al. "FSTL3 deletion reveals roles for TGF-b family ligands in glucose and fat homeostatsis in adults," PNAS (Jan. 23, 2007), vol. 104, No. 4, pp. 1348-1353.
International Preliminary Report on Patentability and English translation of Written Opinion issued Dec. 13, 2012, in PCT International Application No. PCT/JP2011/062296.

* cited by examiner

*Primary Examiner* — Brian J Gangle
*Assistant Examiner* — Andrea McCollum
(74) *Attorney, Agent, or Firm* — Birch, Stewart, Kolasch & Birch, LLP

(57) ABSTRACT

Provided are a means for the prevention and treatment of obesity and/or insulin resistance and, particularly, pharmaceutical drugs for the treatment of obesity and/or insulin resistance under the influence of Follistatin-like 3 (FSTL3). Specifically, provided is an insulin resistance improving drug comprising an FSTL3 inhibitor as an active ingredient, particularly, the insulin resistance improving drug, wherein the FSTL3 inhibitor is one of (A) a substance specifically binding to FSTL3 to inhibit or suppress a function of FSTL3, (B) an inhibitor for expression of FSTL3, and (C) a competitor of FSTL3.

4 Claims, 8 Drawing Sheets

SEQUENCE LISTING

```
<160> NUMBER OF SEQ ID NOS: 3

<210> SEQ ID NO 1
<211> LENGTH: 24
<212> TYPE: DNA
<213> ORGANISM: Artificial
<220> FEATURE:
```

-continued

```
<223> OTHER INFORMATION: antisense oligo

<400> SEQUENCE: 1
ggguuggaag gtactgggca gggc                                           24

<210> SEQ ID NO 2
<211> LENGTH: 24
<212> TYPE: DNA
<213> ORGANISM: Artificial
<220> FEATURE:
<223> OTHER INFORMATION: control oligo

<400> SEQUENCE: 2
cgggacgggt catggaaggu uggg                                           24

<210> SEQ ID NO 3
<211> LENGTH: 236
<212> TYPE: PRT
<213> ORGANISM: Homo sapiens

<400> SEQUENCE: 3
```

Gly Ser Gly Asn Pro Ala Pro Gly Gly Val Cys Trp Leu Gln Gln Gly
1               5                   10                  15

Gln Glu Ala Thr Cys Ser Leu Val Leu Gln Thr Asp Val Thr Arg Ala
            20                  25                  30

Glu Cys Cys Ala Ser Gly Asn Ile Asp Thr Ala Trp Ser Asn Leu Thr
        35                  40                  45

His Pro Gly Asn Lys Ile Asn Leu Leu Gly Phe Leu Gly Leu Val His
    50                  55                  60

Cys Leu Pro Cys Lys Asp Ser Cys Asp Gly Val Glu Cys Gly Pro Gly
65                  70                  75                  80

Lys Ala Cys Arg Met Leu Gly Gly Arg Pro Arg Cys Glu Cys Ala Pro
                85                  90                  95

Asp Cys Ser Gly Leu Pro Ala Arg Leu Gln Val Cys Gly Ser Asp Gly
            100                 105                 110

Ala Thr Tyr Arg Asp Glu Cys Glu Leu Arg Ala Ala Arg Cys Arg Gly
        115                 120                 125

His Pro Asp Leu Ser Val Met Tyr Arg Gly Arg Cys Arg Lys Ser Cys
    130                 135                 140

Glu His Val Val Cys Pro Arg Pro Gln Ser Cys Val Val Asp Gln Thr
145                 150                 155                 160

Gly Ser Ala His Cys Val Val Cys Arg Ala Ala Pro Cys Pro Val Pro
                165                 170                 175

Ser Ser Pro Gly Gln Glu Leu Cys Gly Asn Asn Asn Val Thr Tyr Ile
            180                 185                 190

Ser Ser Cys His Met Arg Gln Ala Thr Cys Phe Leu Gly Arg Ser Ile
        195                 200                 205

Gly Val Arg His Ala Gly Ser Cys Ala Gly Thr Pro Glu Glu Pro Pro
    210                 215                 220

Gly Gly Glu Ser Ala Glu Glu Glu Asn Phe Val
225                 230                 235

INSULIN-RESISTANCE-IMPROVING DRUG

TECHNICAL FIELD

The present invention relates to the prevention and treatment of obesity and/or insulin resistance and particularly to pharmaceutical drugs for the treatment of obesity and/or insulin resistance under the influence of Follistatin-like 3 (FSTL3).

BACKGROUND ART

Obesity is one of root causes of the onset of diabetes. A large number of obese individuals develop a peripheral resistance (insulin resistance) to the action of insulin before the onset of diabetes. It has been indicated that changes in the expression of various adipokines secreted from fat tissues is involved with the induction of insulin resistance. Enlargement of adipocytes is recognized in obese individuals and it has been known that enlarged adipocytes secrete a large amount of adipokines such as cytokines like TNF-α and resistin and free fatty acid and that the adipokines block the transduction of insulin signals in skeletal muscle and liver, inducing insulin resistance (Non-Patent Literatures 1 and 2).

From recent studies, it is believed that although inactive M2 macrophages produce IL-10, which is an anti-inflammatory cytokine, and arginase which suppresses NO biosynthesis to suppress inflammatory changes in non-obese visceral fat tissues, if active M1 macrophages increase due to obesity, inflammatory cytokines such as TNF-α and IL-6 are secreted, promoting inflammatory changes in fat tissues.

It is known that M1 macrophages are almost unrecognizable in non-obese visceral fat tissues while the number of infiltrating M1 macrophages increases due to obesity. M1 macrophages in fat tissues strongly express inflammatory cytokines such as TNF-α, IL-6, and MCP-1, and oxidative stress-related genes such as iNOS. Therefore, it is believed that M1 macrophages promote chronic inflammation and oxidative stress of visceral fat tissues and play an important role in the onset of insulin resistance due to obesity.

In non-obese fat tissues, M2 macrophages are diffusely present. The number of M2 macrophages does not increase due to obesity. Although few reports have been made on the effect of M2 macrophages on insulin sensitivity, it is inferred that M2 macrophages are involved with maintenance/improvement of insulin sensitivity. It has been reported that M2 macrophages strongly express genes different from M1 macrophages, such as IL-10, arginase-1, Mrc1, YM1, and CD209, and that one of anti-inflammatory cytokines, IL-10, enhances insulin signaling in cultured adipocytes (Non-Patent Literature 3). Arginase, which is strongly expressed in M2 macrophages, acts competitively to iNOS. Since the oxidative stress of obese fat tissues promotes insulin resistance, it is thought that M2 macrophages highly expressing arginase are likely to be involved with improvement of insulin resistance.

A molecular mechanism of insulin signal transduction is under extensive study. Pathways called as insulin signal transduction pathways are normally known as a signal transduction system (PI3K-Akt system) from binding of insulin to an insulin receptor causing autophosphorylation of the receptor and leading to IRS (insulin receptor substrate), PI3K (Phosphoinositide 3 kinase), and Aid, and a pathway (MAPK pathway) from binding of insulin to an insulin receptor causing autophosphorylation of the receptor and going through activation of MAPK (mitogen-activated protein kinase). The PI3K-Akt system is thought to be important for changes in glucose metabolism.

A biguanide agent, which mainly suppresses gluconeogenesis in liver, and a thiazolidine derivative, which improves insulin sensitivity in muscles and fat tissues, have been developed as pharmaceutical agents improving insulin resistance and already been approved and used as antidiabetic drugs. The thiazolidine derivatives represented by pioglitazone are believed to activate as a ligand a peroxisome proliferator-activated receptor (PPAR) that is a nuclear receptor transcription factor, induce small adipocytes with high insulin sensitivity from enlarged adipocytes, and promote differentiation of adipocytes, thereby improving the insulin resistance (Non-Patent Literatures 4 to 7). Reports have also been made that indicate a possibility of an antagonist of PPARγ to improve the insulin resistance (Non-Patent Literatures 8 to 10). In addition, the followings have been disclosed as insulin resistance improving agents: an agent for improving insulin resistance containing adiponectin or a gene thereof as an active ingredient (Patent Literature 1); a preventive and/or therapeutic agent for diseases caused by insulin resistance containing a substance having affinity to bombesin receptor subtype 3 (BRS-3) as an active ingredient (Patent Literature 2); a free fatty acid (FFA) reducing agent containing a pyrrole derivative as an active ingredient (Patent Literature 3), etc.

Although various insulin resistance improving drugs have been reported as described above, the causes of obesity and insulin resistance have not yet completely been clarified, and it is desired to clarify unknown pathways or mechanisms leading to obesity or insulin resistance and to develop new pharmaceutical drugs targeting such pathways or mechanisms.

CITATION LIST

Patent Literature

Patent Literature 1: International Publication Pamphlet No. 2003/63894
Patent Literature 2: Japanese Laid-Open Patent Publication No. 10-298100
Patent Literature 3: Japanese Laid-Open Patent Publication No. 08-012573

Non Patent Literature

Non-Patent Literature 1: J. Clin. Invest., 101, pp. 1354-1361, (1998)
Non-Patent Literature 2: J. Biol. Chem., 276, pp. 41245-41254, (2001)
Non-Patent Literature 3: J. Clin. Invest., 117, 175-184, (2007)
Non-Patent Literature 4: J. Biol. Chem., 270, pp. 1295-1299, (1995)
Non-Patent Literature 5: Endocrinology, 137, pp. 4189-4195, (1996)
Non-Patent Literature 6: Trends Endocrinol. Metab., 10, pp. 9-13, (1999)
Non-Patent Literature 7: J. Clin. Invest., 101, pp. 1354-1371, (1998)
Non-Patent Literature 8: Proc. Natl. Acad. Sci., 96, pp. 6102-6106, (1999)
Non-Patent Literature 9: J. Biol. Chem., 275, pp. 1873-1877, (2000)
Non-Patent Literature 10: J. Clin. Invest., 108, pp. 1001-1013, (2001)

SUMMARY OF INVENTION

Technical Problem

It is an object of the present invention to provide a means for the prevention and treatment of obesity and/or insulin resistance, and particularly, new pharmaceutical drugs targeting conventionally unknown pathways or mechanisms leading to obesity or insulin resistance.

Solution to Problem

The present invention is configured as follows.

(1) An insulin resistance improving drug comprising an FSTL3 inhibitor as an active ingredient.

(2) The insulin resistance improving drug of (1), wherein the FSTL3 inhibitor is any one of:

(A) a substance specifically binding to FSTL3 to inhibit or suppress the function of FSTL3;

(B) an inhibitor for the expression of FSTL3; or (C) a competitor of FSTL3.

(3) An insulin resistance improving drug comprising (A), (B), or (C) of (2) above and a pharmaceutically acceptable diluent or carrier.

(4) Use of one or more of (A), (B), or (C) of (2) above in the manufacture of a medicament for inhibiting FSTL3.

(5) Use of one or more of (A), (B), or (C) of (2) above in the manufacture of a composition used for the treatment of insulin resistance in animal or human.

(6) A method of screening a compound for preventing or treating obesity or insulin resistance comprising the steps of:

(i) bringing a test compound into contact with FSTL3-expressing cells; and (ii) confirming whether the test compound improves the inhibition of signal transduction due to FSTL3.

BRIEF DESCRIPTION OF DRAWINGS

FIG. 1-2 shows a result of examination of expression of adipokines in adipocytes when recombinant adenovirus was used for causing B6 mice to express FSTL3.

FIG. 1-3 shows a result of examination of tissue-specific expression of FSTL3 mRNA in control mice and db/db mice with Northern blotting.

FIG. 1-4 shows a result of measurement of Akt phosphorylation in liver and skeletal muscle when FSTL3 antisense oligonucleotides are administered to db/db mice.

FIG. 2-1 shows a result of a glucose tolerance test (GTT) of db/db mice administered FSTL3 antisense oligonucleotides and control db/db mice.

FIG. 2-2 depicts that the expression of FSTL3 mRNA rises in mice becoming obese due to feeding of high-fat diet.

FIG. 2-3 shows a result of a glucose tolerance test (GTT) when recombinant adenovirus is used for causing db/db mice and high-fat diet-fed B6 mice to express activin B.

FIG. 2-4 shows a result of an insulin tolerance test (ITT) when an anti-FSTL3 antibody is administered to db/db mice.

DESCRIPTION OF EMBODIMENTS

Figure 1:
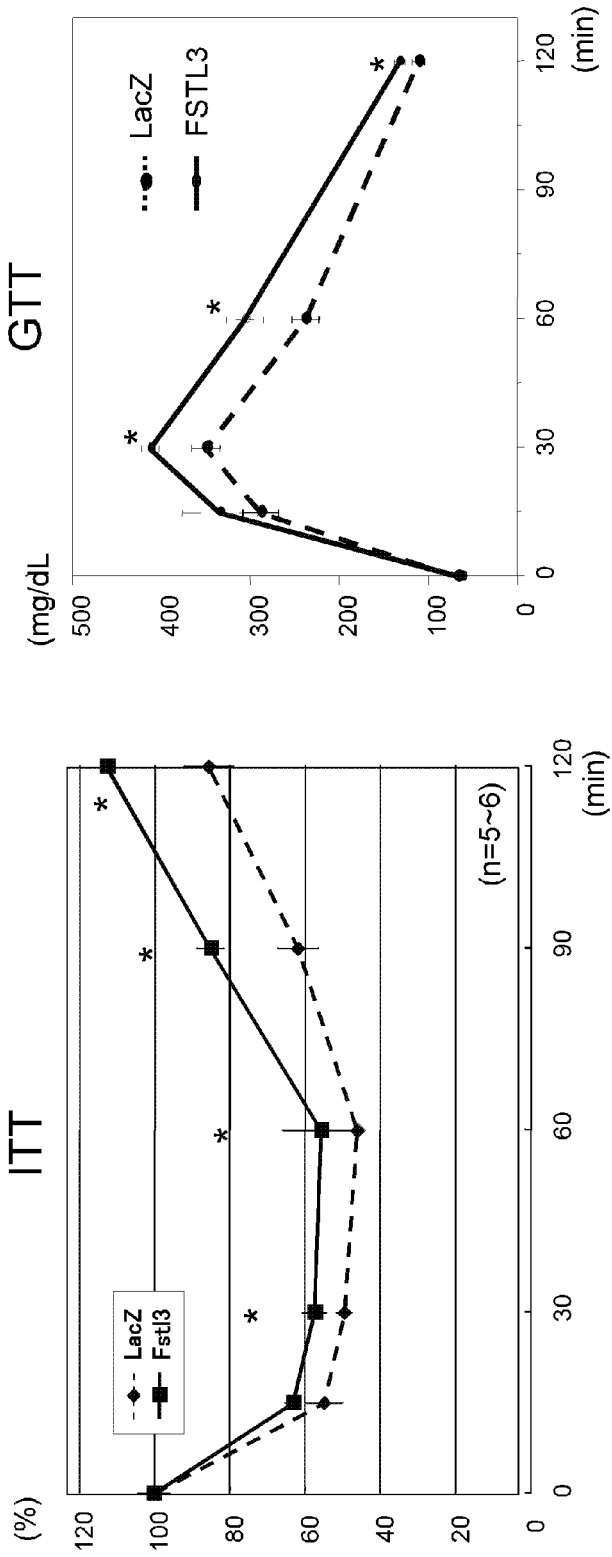
FIG. 1-1 shows results of an insulin tolerance test (ITT) and a glucose tolerance test (GTT) when recombinant adenovirus was used for causing B6 mice to express FSTL3.

In view of the above background, the inventors have performed a global analysis of gene expression in adipocytes derived from humans with various BMI values so as to clarify unknown pathways or mechanisms leading to obesity or insulin resistance. As a result, the inventors have revealed new findings that the expression of FSTL3 gene was increased in obese humans with a BMI value equal to or greater than 25 and in humans having insulin sensitivity reduced (insulin resistance deteriorated) regardless of a BMI value less than 25. Moreover, the inventors have closely studied the relationship between the variation of FSTL3 expression and insulin resistance to confirm that FSTL3 is involved with the induction of obesity and/or insulin resistance. The present inventors have conducted further study to discover that new pharmaceutical drugs targeting previously unknown pathways or mechanisms leading to obesity or insulin resistance could be provided, thereby completing the present invention. The present invention will hereinafter be described in detail.

In this description, the terms have the following meanings.

(Obesity)

Obesity refers to the case of a BMI (Body Mass Index) value equal to or greater than 25 in humans. A BMI value is indicated by $(\text{body weight (kg)})/(\text{body height (m)})^2$.

(Insulin Resistance)

"Insulin resistance" or "reduction in insulin sensitivity" refers to reduction in sensitivity of body tissues to the action of insulin as compared to an "expected" or "normal" value related to the action of insulin. More specifically, insulin resistance is defined as impairment in biological responsiveness to either exogenous insulin or endogenous insulin. If insulin resistance or reduction in insulin sensitivity exists, time-dependent reduction in blood glucose level is diminished in a glucose tolerance test or reduction in blood glucose level does not occur in accordance with insulin intake in an insulin tolerance test. Therefore, such events may be used as indicators of insulin resistance.

(Treatment and Prevention of Insulin Resistance)

The treatment and prevention of insulin resistance include changing insulin resistance toward insulin sensitivity and changing insulin resistance toward glucose transport activity. Specifically, the treatment and prevention of insulin resistance include the control of inhibition action for the transduction of insulin signals in insulin resistance. The treatment and prevention of insulin resistance may, for example, be the treatment of a disease associated with insulin resistance.

(Follistatin-Like 3: FSTL3)

"FSTL3" is a secretory glycoprotein binding to activin (Tsuchida et al., J. Biol. Chem. 275: 40788-96 (2000); Hill et al., J. Biol. Chem. 277: 40735-41 (2002)). This protein consists of a signal peptide and two tandem segments including a follistatin-like domain (SMART accession SM00274) and a Kazal-like serine protease inhibitor domain (SMART accession SM00280). FSTL3 is mainly expressed in placenta, ovary, uterus, and testis and is also expressed in tissues of skin, heart, lung, and kidney.

(FSTL3 Inhibitor)

"FSTL3 inhibitor" means a substance inhibiting or blocking the function or action of FSTL3 inducing obesity and/or insulin resistance. Typical substances include (A) a substance specifically binding to FSTL3 to inhibit or suppress the function or action of FSTL3, (B) an inhibitor for expression of FSTL3, and (C) a substance inhibiting or suppressing the function of FSTL3 through competition with FSTL3.

A specific example of (A) above may be an FSTL3 binding protein, an antibody for FSTL3, or a fragment having antigen-binding activity thereof; a specific example of (B) above may be an antisense oligonucleotide and siRNA of FSTL3, a chemically-modified version thereof, and an FSTL3 expression inhibiting drug; and a specific example of (C) above may be an FSTL3 fragment and an FSTL3 homologue lacking the function or action of FSTL3 inducing obesity and/or insulin resistance.

Substance specifically binding to FSTL3 to inhibit or suppress the function or action of FSTL3 ("FSTL3 inhibitor" (A)) will further be described. The substance specifically binding to FSTL3 to inhibit or suppress the function or action of FSTL3 ("FSTL3 inhibitor" (A)) designed in accordance with the following guideline can preferably be used as a test compound (candidate compound) of the screening method of the present invention.

The "FSTL3 inhibitor (A)" includes not only natural or endogenous FSTL3 binding proteins but also a protein (such as a recombinant and synthetic protein) having the same amino-acid sequence as the natural or endogenous FSTL3 binding proteins, a variant maintaining the same activity as original protein (e.g., a variant acquired by deletion, substitution, or insertion of one or more amino acids), and a protein and peptide that may bind to FSTL3 to inhibit the transduction of insulin signals. An antibody will hereinafter be described as an example.

(i) Antibody

An "antibody" used in the present invention has an avidity for a specific binding partner of FSTL3 or an activity inhibiting or suppressing a function of FSTL3, such as signal transduction-inhibiting activity. Such an antibody can selectively inhibit the function of FSTL3, and thus, can improve insulin resistance due to FSTL3. In the present invention, an antibody may be either a polyclonal or a monoclonal antibody. An antibody or a peptide fragment having antigen-binding activity thereof may be applicable and an antibody may be manufactured by using a DNA immunization method or a gene-recombination technique as well as a manufacturing method using an immunization method of administering an antigen well-known to those skilled in the art.

An antibody recognizing FSTL3 and an antibody neutralizing the activity thereof can be acquired by appropriately immunizing animals with common procedures by using an FSTL3 protein acting as an antigen, a peptide fragment including an epitope thereof, etc. A commercially available antibody (e.g., FLRG(N-18) manufactured by Santa Cruz) may be used. The amino-acid sequence of FSTL3 and the nucleotide sequence coding the amino acids are known and the nucleotide and amino-acid sequence of human FSTL3 is registered as the accession numbers NM_005860 and AAQ89276, respectively, in the database of NCBI, as described above. Based on these sequences, an antigenic peptide can be synthesized to make an antibody (polyclonal or monoclonal antibody) thereto. An anti-FSTL3 antibody of the present invention is useful for the treatment of obesity and/or insulin resistance.

Manufacturing methods of polyclonal and monoclonal methods are well-known to those skilled in the art. For example, references can be made to a large number of literatures such as *Antibodies: A laboratory Manual*, ed. by Lane, H, D. et al., Cold Spring Harbor Laboratory Press, New York, 1989; Kohler et al., *Nature,* 256: 495-497 (1975); and *Eur. J. Immunol.* 6: 511-519 (1976); Milstein et al., *Nature* 266: 550-552 (1977); and Koprowski et al., U.S. Pat. No. 4,172, 124.

Typical antibody manufacturing methods will hereinafter exemplarily be described.

(1) Polyclonal Antibody

To acquire a polyclonal antibody for a certain protein or peptide fragment thereof, an animal is generally immunized by using the protein or peptide as an antigen. The immunization is performed by intravenous, subcutaneous, or intraperitoneal administration to a mammal (e.g., rat, mouse, rabbit, or human). Intervals of the immunization are not particularly limited and the immunization is performed one to ten times, preferably, four to five times, at intervals of two to three weeks. An antibody titer is measured after seven to ten days from the last immunization day and blood is collected on the day of the highest antibody titer to acquire antiserum. The antibody titer can be measured by an enzyme-linked immunosorbent assay (ELISA), a radioimmunoassay (RIA), an immunohistochemical staining, etc. If an antibody must be purified from antiserum, the purification can be performed by appropriately selecting a known method such as ammonium sulfate precipitation, ion-exchange chromatography, gel filtration, and affinity chromatography or by a combination thereof.

(2) Monoclonal Antibody

1) Immunization

To acquire a monoclonal antibody, an animal is generally immunized by using an antigen protein or a peptide fragment thereof. The immunization is performed by intravenous, subcutaneous, or intraperitoneal administration to a mammal (e.g., rat or mouse). One dose of antigen is 30 μg per body in the case of mouse. Intervals of the immunization are not particularly limited and the immunization is performed at least four to five times at intervals of several days to several weeks, preferably at intervals of two to three weeks. After the last immunization, antibody-producing cells are collected. The antibody-producing cells are preferably spleen cells.

2) Cell Fusion

Cell fusion is then performed between the antibody-producing cells such as spleen cells and myeloma cells. Widely available established cells derived from an animal such as a mouse can be used for the myeloma cells. Preferably, a cell line used is selectable with drug and is inviable in an unfused state and viable only when fused with the antibody-producing cells in the HAT selection medium (containing hypoxanthine, aminopterin, and thymidine). For example, specific examples of myeloma cells are mouse myeloma cell lines such as P3X63-Ag and X63Ag8.653. Cell fusion is performed by mixing the antibody-producing cells and the myeloma cells at a predetermined ratio (e.g., 3:1) in an animal cell culture medium such as DMEM and RPMI-1640 medium not containing serum in the presence of a cell fusion promoter such as polyethylene glycol or with electric pulse processing (e.g., electroporation).

3) Selection of Hybridomas

Hybridomas are selected. For example, cells are cultured by using a medium containing hypoxanthine (100 μM), aminopterin (0.4 μM), and thymidine (16 μM) and the grown cells may be acquired as hybridomas. Screening is performed to check whether a desired antibody exists in culture supernatant of the grown hybridomas. The screening of hybridomas may be performed in accordance with a normal method and is not particularly limited. For example, a portion of culture supernatant contained in a well with cells grown as hybridomas can be collected and screening can be performed by an immunostaining method, an enzyme-linked immunosorbent assay (ELISA), a radioimmunoassay (RIA), etc.

4) Cloning

The fused cells are cloned by a limiting dilution method etc., to finally establish hybridomas that are monoclonal antibody-producing cells. To collect the monoclonal antibody from the establish hybridomas, a normal cell culturing method etc., can be employed. Under the cell culturing method, the hybridomas are cultured in an animal cell culture medium such as 10% fetal bovine serum containing RPMI-1640 medium or MEM medium under a normal culture condition (e.g., 37° C., 5% $CO_2$ concentration) for, for example, 14 days to acquire the monoclonal antibody from culture supernatant thereof.

5) Purification

If an antibody must be purified, the purification can be performed by appropriately selecting a known method such as ammonium sulfate precipitation, ion-exchange chromatography, affinity chromatography, and gel chromatography or by a combination thereof.

(3) Another Antibody Manufacturing Method

The antibody can also be acquired by selection from an antibody library consisting of phage vectors or similar vectors (Huse et al., (1989) "Generation of a Large Combinatorial Library of the Immunoglobulin Repertoire in Phage-Lambda", *Science* 246: 1275-1281; and Ward et al., (1989) *Nature* 341: 544-546).

(4) Modification of Antibody

The antibody may be in the form of a chimeric antibody or humanized antibody. When applied to humans in particular, the antibody is preferably humanized to minimize immune reaction. A method for preparing such a humanized antibody is known to those skilled in the art. The antibody may be labeled by using a detectable label such as a radionuclide, an enzyme, a substrate, a cofactor, an inhibitor, a fluorescent label, a chemiluminescent label, and a magnetic particle as needed depending on the purpose.

(ii) Others

The substance specifically binding to FSTL3 to inhibit or suppress the function or action of FSTL3 ((A) above) can be a substance other than antibody on the condition that the substance can specifically bind to FSTL3 to inhibit or suppress the function of FSTL3. Such a substance may be activin species, polymer, or chemical reagent.

An example of screening method of the substance specifically binding to FSTL3 to inhibit or suppress the function or action of FSTL3 ((A) above) may be a method in which primary screening is performed by examining the ability to bind to FSTL3 as a first indicator so as to subsequently determine whether a candidate compound extracted by the first screening has desired inhibiting activity by utilizing an appropriate biological assay. Objects of screening in this case include low-molecular substances. An example of the biological assay can be a method using as an indicator an activity which lies downstream of the insulin signal transduction pathway.

The followings are examples of the biological assay.

A candidate compound is administered to a db/db mouse, a high-fat diet-fed mouse, and a mouse with an FSTL3 gene expression level increased by genetic engineering etc., to perform ITT or GTT.

Real-time PCR, northern blotting, etc., are used for checking a reduction in expression level of M1 macrophage markers such as IL-6 and TNF-α or an increase in expression level of M2 macrophage markers such as arginase.

Western blotting etc., are used for measuring phosphorylated Akt in liver or skeletal muscle.

Specific procedures of these assays will be obvious to those skilled in the art by reference to Examples of this description.

An inhibitor for expression of FSTL3 ("FSTL3 inhibitor" (B)) will further be described. An inhibitor for expression of FSTL3 ("FSTL3 inhibitor" (B)) designed in accordance with the following guideline can preferably be used as a test compound (candidate compound) of the screening method of the present invention.

(i) Antisense of FSTL3

The term "antisense oligonucleotide (antisense)" as used herein means a DNA within the antisense strand of double-stranded DNA or an RNA corresponding to the DNA within the antisense strand, which binds to DNA or RNA to adjust expression of FSTL3. Antisense oligonucleotide can be manufactured as DNA based on the nucleotide sequence of a gene coding FSTL3 protein or manufactured as RNA by incorporating the DNA into an expression plasmid in the direction of antisense, for example. Although the antisense oligonucleotide may have a sequence complementary to a DNA segment of any region of the coding and 5' non-coding sequence of FSTL3 DNA, the antisense oligonucleotide desirably has a sequence complementary to the transcriptional start site, the translation start site, a 5' non-translated region, a boundary region between exon and intron, or the 5' CAP region.

(ii) siRNA (Short Interfering RNA) of FSTL3

An siRNA of FSTL3 is a short double-stranded RNA homologous to the mRNA of FSTL3 and having about 21 to 25 bases with protruding 3' ends on both sides. The siRNA can be synthesized by using cDNA of FSTL3 as a template. The siRNA used in the present invention may have the same relationship to the nucleotide sequence of FSTL3 as the antisense oligonucleotide has to the nucleotide sequence of FSTL3.

(iii) Chemically Modified Version of Antisense and siRNA of FSTL3

A chemical modification of FSTL3 antisense oligonucleotide may be a derivative which is modified for increasing the transferability of DNA or RNA into cells or the stability thereof in cells and, for example, a derivative of phosphorothioate, phosphorodithioate, alkylphosphotriester, alkylphosphonate, or alkylphosphoramidate ("*Antisense RNA and DNA*", WILEY-LISS, 1992, P.1-50). The chemically modified version can be manufactured in accordance with a method described in the literature etc. Insulin resistance can be improved by using the antisense oligonucleotide or the chemically modified version thereof to control expression of the gene coding FSTL3 protein. If the antisense oligonucleotide or the chemically modified version thereof is directly administered, the antisense oligonucleotide preferably has, for example, a length of 5 to 200 bases, more preferably 10 to 50 bases, particularly preferably 15 to 30 bases.

(iv) Method of Utilizing Antisense of FSTL3

If an antisense oligonucleotide is incorporated into an expression plasmid, a preferable length of the antisense oligonucleotide is equal to or less than 1,000 bases, preferably equal to or less than 500 bases, more preferably equal to or less than 150 bases. After the incorporation of the antisense oligonucleotide into an expression plasmid, introduction into target cells is performed in accordance with a common method. The introduction can be performed by a method utilizing liposome, recombinant virus, etc. The expression plasmid of the antisense oligonucleotide can be produced by using a normal expression vector through linkage to the downstream of a promoter in reverse direction, i.e., such that the FSTL3 gene is transcribed in the direction from 3' to 5'.

(v) Method of Utilizing siRNA of FSTL3

When introduced into a cell, the siRNA recognizes and cuts the target mRNA in a sequence specific manner to suppress expression of the target gene. The siRNA can be introduced directly into a cell or can be incorporated into an siRNA expression vector before introduction (reference: "*RNAi Experimental Protocol*" Yodosha).

If an antisense oligonucleotide, a chemically modified version of an antisense oligonucleotide, or an siRNA is directly administered, it may be mixed and prepared with a stabilizer, a buffer, a solvent, etc., and then administered concurrently with an antibiotic, an anti-inflammatory agent, an anesthetic drug, etc. Pharmaceutical agents created in this way can be administered in various ways. The administration is preferably performed on consecutive days or every several days or several weeks. A normal dosage can be changed as needed depending on the seriousness of symptoms.

A substance inhibiting or suppressing the function of FSTL3 through competition with FSTL3 ("FSTL3 inhibitor" (C)) will further be described.

The FSTL3 inhibitor (C) is not particularly limited as long as it competes, in the context of the variation of FSTL3 and the insulin resistance, with a potential interacting partner of FSTL3 (e.g., activins) and, if present, inhibits the function or action of FSTL3 which would have been exerted in the absence of the FSTL3 inhibitor (C). Not to mention that the FSTL3 inhibitor (C) should have no substantial adverse effect on the maintenance of homeostasis of insulin sensitivity (activity of the insulin signal transduction pathway) of the potential interacting partner of FSTL3. Specifically, the FSTL3 inhibitor (C) include: a peptide fragment derived from FSTL3 (hereinafter sometimes simply referred to as "FSTL3 peptide fragment") or an FSTL3 homologue lacking action on the potential interacting partner of FSTL3; and an anti-activin antibody binding to an FSTL3-binding site within the molecule of an activin. The FSTL3 inhibitor (C) is different from the FSTL3 inhibitor (A) in that binding to FSTL3 is not necessary.

The term "homologue" as used herein refers to a peptide retaining a side-chain structure similar to a normal natural peptide (i.e., a prototype) although a difference from the natural peptide is generated by slight modification made to the natural peptide. Such a change includes, but not limited to, a change occurring in one to several amino-acid side chains; a change in one to several amino acids including deletion (e.g., a truncated peptide), insertion, and/or substitution; a change in stereochemistry of one to several atoms; and/or moderate derivatization including methylation, glycosylation, phosphorylation, acetylation, myristoylation, prenylation, palmitation, amidation, and/or addition of glycosylphosphatidylinositol. Although a homolog preferably has enhanced or substantially the same characteristics as compared to the natural peptide, a peptide having characteristics antagonistic to the activity of the natural peptide is also included in a certain embodiment of the present invention.

With regard to whether a peptide fragment of FSTL3 or an FSTL3 homologue is "(C) a substance inhibiting or suppressing the function of FSTL3 through competition with FSTL3", a compound can be screened by utilizing an appropriate biological assay and using as an indicator an activity of a signal transduction pathway which lies on the downstream of a signal transduction pathway. For example, only FSTL3, only a candidate compound, or FSTL3 and the candidate compound can be added to a cultured cell system having a receptor of FSTL3 forcibly expressed, thereby determining whether the candidate compound has desired inhibitory activity.

(Assay for Determining Whether Candidate Compound is an Inhibitor (A) of the Present Invention)

To determine whether a candidate compound of the "FSTL3 inhibitor" is "(A) a substance specifically binding to FSTL3 to inhibit or suppress the function of FSTL3", for example, the determination is achieved by (1) confirming the specific binding between the candidate compound and FSTL3 and (2) confirming the inhibition or suppression of the function of FSTL3 by the candidate compound.

(1) Confirmation of Specific Binding Between Candidate Compound and FSTL3

A specific method of confirming the specific binding between the candidate compound and FSTL3 can be an ELISA method or a Biacore® method based on the principle of the surface plasmon resonance phenomenon (SPR).

(2) Confirmation of Inhibition or Suppression of Function of FSTL3 by Candidate Compound A method of confirming the inhibition or suppression of the function of FSTL3 by the candidate compound can be any method capable of detecting expression of FSTL3 on the gene level or the protein level.

In other words, all that is required is to determine on the gene level or the protein level that the presence of the candidate compound reduces the gene expression level of IL-6 or TNF-α gene the expression of which is induced by the signal transduction due to FSTL3.

Description will hereinafter be made of the case that "(A) a substance specifically binding to FSTL3 to inhibit or suppress the function of FSTL3" is an anti-FSTL3 antibody.

(i) Antibody Specifically Binding to FSTL3 (Anti-FSTL3 Antibody)

The anti-FSTL3 antibody acquired by the manufacturing method above is directly labeled or used as a primary antibody for detection in cooperation with a labeled secondary antibody (recognizing an antibody derived from animal used for producing the antibody) specifically recognizing the primary antibody.

For the labeling, for example, a detectable substance such as an enzyme label, a radioactive label, and a fluorescent label is used. Specifically, enzymes such as horseradish peroxidase, alkaline phosphatase, and β-D-galactosidase, radioactive isotopes such as $^{125}$I, light-emitting materials such as an acridinium compound and luminol, fluorescent materials such as fluorescein isothiocyanate or europium(III) chelate, etc., are known, and known methods are usable without limitation for a method of labeling an antibody (method of introducing or binding a labeling-material).

(ii) Production of Solid-Phased Plate

In a method of solid-phasing FSTL3, for example, an FSTL3 diluted solution (e.g., a solution diluted by phosphate buffered saline (hereinafter referred to as "PBS") containing 0.05% sodium azide) is put into a 96-well plate (such as Immunoplate MAXISORP® (manufactured by NUNC®)) and allowed to stand still at 4° C. to room temperature overnight or at 37° C. for 1 to 3 hours so as to adsorb FSTL3 on well bottom surfaces.

(iii) Detection

To prevent nonspecific adsorption of antibodies onto the surfaces of the well bottom of the plate on which a sample is solid-phased, a buffer solution containing a substance inhibiting the nonspecific adsorption (such as skim milk, casein, bovine serum albumin, gelatin, and polyvinyl pyrrolidone) is dispensed into wells in advance and allowed to stand still for a certain period of time (blocking). For composition of the blocking solution, for example, phosphate buffered saline (PBS) or Tris-buffered saline (TBS) containing 5% skim milk and 0.05 to 0.1% TWEEN 20® (polysorbate 20) is used. A blocking reagent, BLOCK ACE®, (manufactured by Dainippon Pharmaceutical), 1 to 10% bovine serum albumin, 0.5 to 3% gelatin, or 1% polyvinyl pyrrolidone may be used instead of skim milk.

After the inside of wells is washed with PBS or TBS containing 0.05 to 0.1% TWEEN 20® (polysorbate 20)(hereinafter referred to as "washing solution") to remove the excess blocking solution, the anti-FSTL3 antibody appropriately diluted with the washing solution is dispensed and incubated for a certain period of time to bind an antigen to the antibody. A dilution rate of the antibody in this case can be determined by conducting a preliminary ELISA experiment using a sample acquired by serially diluting the recombinant antigen mentioned above. This antibody reaction operation is preferably performed at room temperature for about one hour.

After the antibody reaction operation is completed, the inside of the wells is washed with the washing solution.

If the antibody used is already labeled, a detection operation can immediately be performed. If an unlabeled antibody is used, a secondary antibody reaction is subsequently performed. For example, if a commercially available labeled secondary antibody is used, the labeled secondary antibody is used after dilution by a factor of 2,000 to 20,000 with the washing solution (if a preferred dilution rate is described in attached instructions, the antibody is diluted as instructed). A secondary antibody solution is dispensed into the wells after washing and removing the primary antibody and incubated at room temperature for 1 to 3 hours, and after washing with the washing solution, a detection operation is performed in accordance with the labeling method.

(iv) The antibody selected at the step above is added to any cultured cells with FSTL3 forcibly expressed by using an any expression plasmid to detect at the gene level or protein level whether suppression or reduction occurs in expression of IL-6 the expression of which is induced or increased by FSTL3. It will be obvious to those skilled in the art that a method described later for FSTL3 is applicable to a method of detecting expression of IL-6.

(Assay for Determining Whether Candidate Compound Corresponds to Inhibitor (B) of the Present Invention)

A method of determining whether a candidate compound of the "FSTL3 inhibitor" is "(B) an inhibitor for expression of FSTL3" may be any method capable of detecting the expression of FSTL3 at (1) the gene level or (2) at the protein level.

(1) Expression Detection at Gene Level

A method of detecting expression at the gene level may be a nucleic-acid hybridization method using a solid-phased sample of a gene chip, a cDNA array, and a membrane filter, as well as an RT-PCR method, a real-time PCR method, etc., and particularly preferable method is an RT-PCR method or a real-time PCR method.

A detection method for the FSTL3 gene may be, for example, a method in which total RNA is extracted from adipocytes to detect the expression level of the FSTL3 gene (mRNA) in the total RNA.

(i) Extraction of Total RNA

The extraction of total RNA is performed by using an RNA extracting solvent from isolated blood or cells in accordance with a known method. The extracting solvent is preferably, for example, a solvent containing a component having an effect of inactivating ribonuclease such as phenol (e.g., TRIZOL® reagent manufactured by Gibco BRL). The RNA extracting method is not particularly limited and can be, for example, a guanidine thiocyanate/cesium chloride ultracentrifugal method, a guanidine thiocyanate/hot phenol method, a guanidine hydrochloric acid method, or an acidic guanidine thiocyanate/phenol chloroform method (Chomczynski, P. and Sacchi, N., (1987) Anal. Biochem., 162, 156-159). Particularly, the acidic guanidine thiocyanate/phenol/chloroform method is preferred.

The extracted total RNA may be purified to acquire only mRNA as needed. Although a purifying method is not particularly limited, a large portion of mRNAs present in the cytoplasm of eukaryotic cells have poly(A) sequence at 3' ends and, therefore, for example, this feature can be used for performing the purification as follows. First, biotinated oligo (dT) probes are added to the extracted total RNA for adsorption of poly(A)$^+$ RNA. Paramagnetic particle carriers with streptavidin immobilized are added for capturing poly(A)$^+$ RNA by utilizing the binding between biotin and streptavidin. After washing operation, poly(A)$^+$ RNA is finally eluted from the oligo(dT) probes. In addition to this method, a purification method using an oligo(dT) cellulose column for adsorption and elution of poly(A)$^+$ RNA may be employed. The eluted poly(A)$^+$ RNA may further be fractionated by a sucrose density-gradient centrifugation method etc.

(ii) Detection for FSTL3 Gene

The expression level of the FSTL3 gene in total RNA is detected under the condition of with or without administration of a test substance. Gene expression level can be detected as signal intensity by preparing cRNA or cDNA from acquired total RNA and labeling the cRNA or cDNA with an appropriate labeling compound. For a detecting method of gene expression level, the RT-PCR method (real-time PCR method) will hereinafter be described.

RT-PCR Method (Real-Time PCR Method)

The RT-PCR method, and particularly the real-time PCR (TAQMAN® PCR) method, are preferred for an evaluation method of the present invention in that a trace amount of DNA can highly sensitively and quantitatively be detected. The real-time PCR (TAQMAN® PCR) method uses an oligonucleotide probe labeled at the 5' end with fluorescent dye (reporter) and the 3' end with a quenching agent (quencher), the probe hybridizing to a certain region of the target gene. In the probe, the fluorescence of the reporter is suppressed by the quencher in a normal state. When the fluorescent probe is completely hybridized to the object gene, Taq DNA polymerase is used from the outside to perform PCR. As elongation due to the Taq DNA polymerase proceeds, the exonuclease activity thereof hydrolyzes the fluorescent probes from the 5' end and the reporter dye is released, producing fluorescence. In the real-time PCR method, the fluorescent intensity can be monitored in real time to accurately determine the initial amount of template DNA. For the real-time monitoring, a LightCycler (registered trademark) 480 System (Roche Diagnostics K.K.) etc., are usable.

For example, in the case of the present invention, primers specifically amplifying the mouse Fstl3 gene (mRNA) and probes specifically detecting the mouse Fstl3 gene are designed to perform the real-time PCR (TAQMAN® PCR). If the expression level of the FSTL3 gene is significantly reduced under the condition of administrating a test substance as compared to the non-administration condition, the test substance can be evaluated to have an FSTL3 inhibiting effect.

(2) Expression Detection on Protein Level

A method of detecting expression at the protein level may be Western blotting method, a dot blotting method, a slot blotting method, an ELISA method, an RIA method etc., and is particularly preferably the western blotting method.

Western blotting method will hereinafter be described as an example.

(i) Preparation of Sample

Adipocytes or cells having FSTL3 or the gene thereof highly expressed are preferable as a sample. These cells (used as cell extract solution) are centrifuged at high speed as needed to remove insoluble substances and prepared into a Western blotting sample as follows.

For the Western blotting (electrophoresis) sample, for example, the cell extract solution is directly used or is appropriately diluted by a buffer solution and mixed with a sample buffer solution (manufactured by Sigma, etc.) containing 2-mercaptoethanol for SDS-polyacrylamide gel electrophoresis.

(ii) Solid-Phasing of Sample

In the method, first, polypeptide in a sample containing FSTL3 is solid-phased on a membrane or bottom surfaces in wells of a 96-well plate. A method of solid-phasing on a membrane can be a method in which polypeptide is transferred on a membrane after polyacrylamide gel electrophoresis of the sample (Western blotting method) or a method in which a membrane is directly impregnated with the sample or a diluted solution thereof (the dot blotting method and the slot blotting method). The membrane used can be a nitrocellulose membrane (e.g., manufactured by Bio-Rad), a nylon membrane (e.g., HYBOND™-ECL (manufactured by Amersham Pharmacia)), a cotton membrane (e.g., Blot Absorbent Filter (manufactured by Bio-Rad)), or a polyvinylidene difluoride (PVDF) membrane (e.g., manufactured by Bio-Rad). A blotting method can be a wet-type blotting method (*Current Protocols in Immunology*, Volume 2, ed. by J. E. Coligan, A. M. Kruisbeek, D. H. Margulies, E. M. Shevach, and W. Strober), a semi-dry-type blotting method (see *Current Protocols in Immunology*, Volume 2, described above), etc.

(iii) Antibody Specifically Binding to FSTL3 (Anti-FSTL3 Antibody)

The anti-FSTL3 antibody used in this step can be produced by the method described above.

The anti-FSTL3 antibody acquired with the method described in (iii) above is directly labeled or used as a primary antibody for detection in cooperation with a labeled secondary antibody specifically recognizing the primary antibody (recognizing an antibody derived from animal used for producing the antibody).

Preferable types of the labeling include, but not limited to, enzymes (alkaline phosphatase or horseradish peroxidase) or biotin (however, if a secondary antibody is used, an operation of binging enzyme-labeled streptavidin to biotin of the secondary antibody is further added). For the labeled secondary antibody (or labeled streptavidin), various types of pre-labeled antibodies (or streptavidin) are commercially available. In the case of RIA, an antibody labeled by a radioactive isotope such as $^{125}$I is used and a liquid scintillation counter etc., are used for measurement.

The expression level of the antigen, FSTL3, is measured by detecting the activity of these labeled enzymes. In the case of labeling with alkaline phosphatase or horseradish peroxidase, substrates developing a color and substrates emitting light due to catalyzation of the enzymes are commercially available.

If a color-developing substrate is used, the detection can visually be performed by utilizing Western blotting method or dot/slot blotting methods. An antigen concentration in a sample can be determined if a dilution series of the antigen used for production of the antibody is prepared and used as standard antigen samples, and then, a detection operation is performed concurrently with the sample to create a standard curve by plotting standard antigen concentrations and the measurement value.

On the other hand, if a light-emitting substrate is used, the detection can be performed by autoradiography using an X-ray film or an imaging plate and by photography using an instant camera. The quantitative determination can also be performed by utilizing densitometry, the Molecular Imager FX system (manufactured by Bio-Rad), etc.

(iv) Measurement Operation

To prevent nonspecific adsorption of antibodies, an operation (blocking) is performed by immersing the membrane in advance into a buffer solution containing a substance preventing the nonspecific adsorption (such as skim milk, casein, bovine serum albumin, gelatin, and polyvinyl pyrrolidone) for a certain period of time. The conditions etc., of the blocking are the same as the ELISA method described above.

After the membrane is washed with a washing solution such as PBS or TBS containing 0.05 to 0.1% TWEEN 20® (polysorbate 20) to remove the excess blocking solution, the anti-FSTL3 antibody is immersed into a solution appropriately diluted with the blocking solution for a certain time period to bind an antigen on the membrane to the antibody. A dilution rate of the antibody in this case can be determined by conducting a preliminary Western blotting experiment using a sample acquired by serially diluting the recombinant antigen. This antibody reaction operation is preferably performed at room temperature for two hours. After the antibody reaction operation is completed, the membrane is washed with the washing solution. If the antibody used is already labeled, the detection operation can immediately be performed. If an unlabeled antibody is used, a secondary antibody reaction is subsequently performed. For example, if a commercially available labeled secondary antibody is used, the labeled secondary antibody is used after dilution by a factor of 2,000 to 20,000 with the blocking solution (if a preferred dilution rate is described in attached instructions, the antibody is diluted as instructed). The membrane after washing and removing the primary antibody is immersed in a secondary antibody solution for 45 minutes to 1 hour at room temperature and washed with the washing solution, and the detection operation is performed in accordance with the labeling method as described above. For example, the washing operation is performed by shaking the membrane in the washing solution for 15 minutes, shaking the membrane for 5 minutes after replacing with the fresh washing solution, and then shaking the membrane for 5 minutes after replacing with the fresh washing solution again. The washing may further be performed after replacing with the fresh washing solution once again as needed.

(Assay for Determining Whether Candidate Compound Corresponds to Inhibitor (C) of the Present Invention)

For a method of determining whether a candidate compound of the FSTL3 inhibitor is "(C) a competitor of FSTL3", any methods are usable as long as it can be confirmed that a candidate compound has both of two characteristics, i.e., a characteristic of (1) binging to activin competitively with FSTL3 and inhibiting formation of an activin-FSTL3 complex and a characteristic of (2) not inhibiting the activity of activin.

Substances with both the characteristic (1) and the characteristic (2) include, for example, an FSTL3 homologue binding to activin but not inhibiting the activin activity, an antibody against an FSTL3-binding site in the molecule of an activin or a fragment thereof not inhibiting binding of activin to activin receptors.

A method of confirming the characteristic (1) may be a BIACORE® method based on the principle of surface plasmon resonance phenomenon (SPR) etc. Among the substances with the characteristic (1), substances with the characteristic (2) can be identified by measuring the expression of IL-6 or TNF-α at the gene level or the protein level.

(i) FSTL3 Homologue

An activin molecule is a dimer and therefore has two activin type I receptor-binding sites and two activin type II receptor-binding sites in one activin molecule, and two molecules of FSTL3 bind to one dimeric activin molecule such that the activin molecule is surrounded, thereby inhibiting the binding of activin to a receptor (*J. Biol. Chem.* 2008 Nov. 21; 283(47): 32831-8). FSTL3 binds to activins at contact points in two discontinuous locations; the first contact point is an N-terminal domain and the contact thereof blocks the activin type I receptor-binding sites; and the second contact points are follistatin domains (FSD) 1 (FSD1) and 2 (FSD2) and the contact thereof blocks the activin type II receptor-binding domain.

The gene and amino-acid sequences of both FSTL3 and activin are already known, and therefore, a nucleotide sequence or amino-acid sequence of a peptide having characteristics of both the characteristic (1) and the characteristic (2) may be designed to acquire the FSTL3 homologue by using an arbitrary gene expression system, a peptide synthesizer, etc., based on information such as the binding sites of FSTL3 and activin, amino-acid or nucleotide sequences, three-dimensional conformations, and electric charges of activin-activin receptor binding sites.

A peptide containing an amino-acid sequence acquired by altering the amino-acid sequence indicated by SEQ ID NO. 3 is preferably used as an example of the FSTL3 homologue used in the present invention. A site to be altered is, for example, from the 49th amino acid (H: histidine) to the 64th amino acid (H: histidine) of the SEQ ID NO. 3 and can be mutated by deletion, substitution, or insertion of at least one or more amino acids.

A peptide containing substantially the same amino-acid sequence as the amino-acid sequence indicated by the SEQ ID NO. 3 is preferably used as an example of the FSTL3 homologue used in the present invention. A site to be altered is, for example, from the 110th amino acid (S: serine) to the 131st amino acid (D: asparagine acid) of the SEQ ID NO. 3 and can be mutated by deletion, substitution, or insertion of at least one or more amino acids.

A peptide containing substantially the same amino-acid sequence as the amino-acid sequence indicated by the SEQ ID NO. 3 is preferably used as an example of the FSTL3 homologue used in the present invention. A site to be altered is, for example, from the 156th amino acid (V: valine) to the 169th amino acid (R: arginine) or from the 194th amino acid (S: serine) to the 210th amino acid (V: valine) of the SEQ ID NO. 3 and can be mutated by deletion, substitution, or insertion of at least one or more amino acids.

If the first to 71st amino acids are altered, preferably, the 72nd to 236th amino acids are not altered, and if the 72nd to 236th amino acids are altered, preferably, the first to 71st amino acids are not altered; however, an alteration can be made in other combinations by using the activin activity as an indicator.

The FSTL3 homologue designed in this way can preferably be used as a test compound (candidate compound) of the screening method of the present invention.

(ii) Anti-Activin Antibody

"(C) a competitor of FSTL3" may be an anti-activin antibody binding to the FSTL3 binding site in the structure of the molecule of an activin and not inhibiting the binding of activin to activin receptors, or a functional fragment of the anti-activin antibody. For example, the anti-activin antibody is produced with a known method by using only a receptor binding site of activin as an antigen. The functional fragment of the antibody can also be acquired with a known method such as a digesting enzyme treatment.

A candidate compound produced as above is added concurrently with an activin and FSTL3 to cultured cells with an activin receptor expressed so as to confirm that the activin activity inhibited by FSTL3 is recovered. For example, variations of expression levels of IL6 and TNF-α, the expression of which is increased by the inhibition due to FSTL3 of activin activity, are measured at the gene level and the protein level to determine whether the candidate compound is (C).

(Administration Method of FSTL3 Inhibitor)

To inhibit or suppress the function of FSTL3 by using the FSTL3 inhibitor of the present invention, an effective amount of the FSTL3 inhibitor is administered solely or in combination with another drug through an appropriate route to a patient requiring treatment etc.

The FSTL3 inhibitor of the present invention may be administered in combination with another therapy and can be used together with a sulfonylurea drug, a phenylalanine derivative (short acting insulin secretagogue), a biguanide, an α-glucosidase inhibitor, a thiazolidine derivative (insulin resistance-improving drug), an insulin formulation, and therapies for various symptoms (e.g., analgesic, diuretic, antidiuretic, antiviral, antibiotic, nutritional supplement, anemia drug, blood-clotting treatment drug, bone treatment drug, and psychiatric and psychological treatment drugs).

A composition containing an FSTL3 binding protein, an antibody to FSTL3, etc., may be mixed with pharmaceutically acceptable appropriate carriers and excipients in a sterilized manner to be prepared as an injection formulation (solution, suspension, emulsion) and an implant formulation, for example. The composition can be administered with an aqueous vehicle, such as water and physiological saline, or various additives and/or excipients. Otherwise, the composition in a buffer solution can be administered without these vehicles, additives, and excipients. Alternatively, the composition may be contained in a suspension such as zinc suspension. Such a suspension can be used for subcutaneous (SC), intradermal (ID), or intramuscular (IM) injection.

An amount of administration of the FSTL3 inhibitor is determined by a clinician based on various factors such as the purpose of treatment and body weight, age, and symptom of the patient. The administration is preferably started from a dose slightly lower than an optimum amount and the dose is gradually increased until a desired effect is achieved while a side effect is monitored. An optimum dosage for treatment can be determined by acquiring a certain amount of sample from the subject and measuring an FSTL3 concentration in the sample. Such a method may be determined as needed by a clinician. The amount of administration varies depending on the FSTL3 inhibitor selected and the seriousness of the symptom to be treated.

(Screening of Compound)

The inventors have revealed that FSTL3 plays an important role in insulin resistance. Therefore, in addition to the screening method, cells expressing the protein can be used for screening a compound (FSTL3 inhibitor) for treating an individual with high expression of FSTL3. Such screening includes (1) a step of bringing a test compound into contact with FSTL3-expressing cells and (2) a step of checking whether the test compound inhibits the function of FSTL3. The FSTL3-expressing cells can be cells of type 2 diabetes-model animals and cells derived from such animals or cells with FSTL3 expressed by incorporating the FSTL3 gene into an appropriate expression vector and introducing the expression vector into host cells. The host cells can be known host cells such as any prokaryotic cells and eukaryotic cells capable of expressing FSTL3. Construction of the expression vector and a transformation method of the host cells are known to those skilled in the art. Whether the function of FSTL3 is inhibited can be determined by utilizing a method of comparing states of insulin signal transduction (e.g., Akt phosphorylation) etc., in the presence and absence of a test compound.

An example of the screening method will hereinafter be described.

"A method of screening a compound for preventing or treating obesity or insulin resistance comprising the steps of:

(1) bringing a test compound into contact with FSTL3-expressing cells; and (2) checking whether the test compound improves the inhibition of signal transduction due to FSTL3."

Although the present invention will hereinafter be described in detail with examples, the present invention is not limited by those examples.

EXAMPLES

Example 1

1. Effect of FSTL3 Overexpression Due to FSTL3 Recombinant Adenovirus Administration on Glucose Metabolism (1) Production of Recombinant Adenovirus and Administration to Mice Full-length mouse FSTL3 cDNA was amplified by using pcDNA3.1/V5-HisA (manufactured by Invitrogen) in accordance with a recommended method. The amplified product was subjected to HindIII and EcoRV treatments and used for production of recombinant adenovirus. The recombinant adenovirus was produced by using TAKARA® Adenovirus Expression Vector Kit (manufactured by TAKARA®) in accordance with a recommended method. For negative control, β-galactosidase gene-containing virus attached to the kit was used. The adenovirus was transfected to HEK293 cells by using CELLPHECT® Transfection Kit (manufactured by GE Healthcare) with the calcium phosphate method. The produced virus was dissolved in 150 μL of PBS to $5.0 \times 10^{10}$ pfu/body and administered to seven-week-old male B6 mice (fed with normal diet) once a week for two weeks.

(2) Insulin Tolerance Test (ITT) and Glucose Tolerance Test (GTT)

ITT and GTT were performed after five days and seven days, respectively, from the last administration. Each of the tests was performed with a group of five to six mice.

(2)-1

Insulin Tolerance Test (ITT)

ITT was performed as follows. Into the abdominal cavities of mice, 3.0 mU/g-BW of insulin (diluted by physiological saline) was continuously administered without fasting. A glucose concentration was measured by a glucose sensor, in this particular instance the Glutest Sensor (from Sanwa Kagaku) from collected whole blood.

(2)-2

Glucose Tolerance Test (GTT)

The GTT was performed as follows. Into the abdominal cavities of mice fasted for 16 hours from the previous day of the test, 1.0 mg/g-BW of glucose (diluted by physiological saline) was administered. Serum was separated from collected whole blood and a glucose concentration was measured by Glucose-Test Wako (manufactured by Wako Pure Chemical Industries).

(3) Result

In the mice administered the virus having the FSTL3 gene in the ITT, a reduction in blood glucose level was obviously smaller as compared to control mice. In the mice administered the virus having the FSTL3 gene in the glucose tolerance test, a significant increase in blood glucose level was confirmed as compared to control mice. From this result, it is found out that FSTL3 induces insulin resistance (see FIG. 1-1).

2. Change in Adipokine Expression in Adipocyte due to FSTL3 Overexpression (1) Production of Recombinant Adenovirus and Administration to Mice Production of recombinant adenovirus and administration to mice were performed with the method described above.

(2) Preparation of RNA

RNEASY® Mini Kit (250) (a RNA purification kit manufactured by Qiagen, Cat. Number 74106) was used for extracting RNA from adipocytes.

(3) Measurement of Adipokines

The RNA extracted at step (2) was used for performing a reverse transcription reaction in accordance with the protocol of High Capacity cDNA Reverse Transcription Kit with RNase Inhibitor (manufactured by ABI®) to perform TAQMAN® PCR. Adiponectin was selected as an M2 macrophage marker and IL-6 and TNF-α were selected as M1 macrophage markers to create respective TAQMAN® probes.

(4) Result

Although no significant change was found in the expression of the M2 macrophage marker, adiponectin, the expression of the M1 macrophage markers, IL-6 and TNF-α, were significantly increased as compared to control. It is indicated that FSTL3 is involved with the induction of insulin resistance through induction of production of inflammatory cytokines in adipocytes (see FIG. 1-2).

3. Change in Akt Phosphorylation Due to Expression Suppression of FSTL3

(1) Administration of Antisense Oligonucleotide

After seven-week-old male db/db mice were adapted for one week, antisense oligonucleotide having the following sequence was intraperitoneally administered twice a week, a total of eight times (total 80 mg/body). The db/db mice were genetic obesity model mice and known to exhibit insulin resistance. It is confirmed by Northern blotting analysis that FSTL3 is highly expressed in adipocytes of the db/db mice as compared to control mice (see FIG. 1-3).

<Oligonucleotide Sequence>

[Chem 1]

Sequence/Modification (= OligoA)
5'-mG*mG*mG*mU*mU*G*G*A*A*G*G*T*A*C*T*G*G*G*C*mA*mG*mG*mG*mC-3'

Control
5'-mC*mG*mG*mG*mA*C*G*G*G*T*C*A*T*G*G*A*A*G*G*mU*mU*mG*mG*mG-3'
(where *= Phosphorothioate Bonds, mN2 = 2'-O-Methyl RNA base(2'-O-Me)

(2) Measurement of Phosphorylation Signals

After 31 days from administration of antisense oligonucleotide, the mice were dissected to extract livers and skeletal muscles and Akt phosphorylation was measured in each of the locations.

(3) Measurement of Akt Phosphorylation

Two-hundred milligram of each of the liver and the skeletal muscle were homogenized in Liver Buffer (having composition described in Table 1) containing 1% NONIDET®-P40 (octylphenoxypolyethoxyethanol). For the liver and the skeletal muscle, 7 mL and 4 mL of the Liver Buffer were respectively used. After centrifugation at 3,000 rpm for 10 minutes at 4° C., the supernatant was dispensed into a tube. The dispensed supernatant was ultracentrifuged at 55,000 rpm for 1 hour at 4° C. and the supernatant was pipetted and dispensed into a tube. After protein determination, SDS-PAGE was performed with 10% gel. After transfer from the gel to a membrane with common procedures, blocking was performed for 30 minutes, and the reaction with a primary antibody (Phospho-Akt (ser473) (cell signaling #92715)) diluted by a factor of 2,000 was performed overnight at room temperature. The reaction with a secondary antibody (goat antiRabbit IgG HRP (Santa Cruz Biotechnology, Inc., sc-2054)) diluted by a factor of 5,000 was performed for 2 hours at room temperature.

TABLE 1

(Composition of Liver Buffer)

| | |
|---|---|
| 10M Tris (pH 7.4) | 12.5 mL |
| 0.5M NaF | 100 mL |
| 100 mM $Na_4P_2O_7$ (PPi) | 250 mL |
| 0.2M EGTA | 25 mL |
| 0.5M EDTA | 10 mL |
| 200 mM PMSF | 5 mL Phenylmetylsulfonyl Fluoride |
| Complete | 10 tabs (Roche 11 697 498 001) |
| $Na_3VO_4$ | 919.6 mg (Sigma S6508, f.c. 10 mM) |
| | 500 mL |

After all the reagents were mixed, pH was adjusted to 7.4. NONIDET®-P40 (octylphenoxypolyethoxyethanol) was added before use in experiments.

(4) Result

In the mice administered the FSTL3 antisense oligonucleotide, Akt phosphorylation due to insulin stimulation exceeding control was identified in both the liver and the skeletal muscles. It was indicated that FSTL3 is involved with the induction of insulin resistance through inhibition of transduction of insulin signals in the PI3K-Akt system (see FIG. 1-4).

Example 2

1. Improvement in Glucose Tolerance through Expression Suppression of FSTL3

(1) Administration of Antisense Oligonucleotide

Administration of antisense oligonucleotide was performed in the same way as the method described above.

(2) Glucose Tolerance Test (GTT)

The GTT was performed after 28 days from the first day of administration. Each test was performed in the same way as the method described above.

(3) Result

In the db/db mice administered the FSTL3 antisense oligonucleotide, a rise in blood glucose level was remarkably suppressed in the glucose tolerance test as compared to control db/db mice and the glucose tolerance was improved. It is indicated that insulin resistance can be improved by suppressing the expression of FSTL3 (see FIG. 2-1).

2. Improvement in Glucose Tolerance through Overexpression of Activin B (1) Production of Recombinant Adenovirus and Administration to Mice The production of adenovirus was performed with the method described above except that full-length mouse inhibin βB cDNA was used.

(2) Administration of Recombinant Adenovirus to db/db mice

After seven-week-old male db/db mice were adapted for one week, $5.0 \times 10^{11}$ pfu/mL of adenovirus was dissolved in 150 μL of PBS and administered from the tail vein once a week for two weeks. GTT was performed on fourth day after the second administration.

(3) Administration of Recombinant Adenovirus to Twelve-Week High-Fat Diet B6 Mice After five-week-old male B6 mice were adapted with normal diet for one week, high-fat diet was fed for twelve weeks. Adenovirus ($5.0 \times 10^{11}$ pfu/mL) was dissolved in 150 μL of PBS and administered to the mice in the 18th week from the tail vein once a week for two weeks. GTT was performed on seventh day after the second administration. The high-fat diet-fed mice were genetic obesity-model mice and known to exhibit insulin resistance. It was confirmed by Northern blotting analysis that FSTL3 is highly expressed in adipocytes of the high-fat diet-fed mice as compared to control mice (see FIG. 2-2).

(4) Glucose Tolerance Test (GTT)

The GTT was performed for the both mice as follows. Into the abdominal cavities of mice fasted for 16 hours from the previous day of the test, 1.0 mg/g-BW of glucose (diluted by physiological saline) was administered. Serum was separated from collected whole blood and the glucose concentration was measured by Glucose-Test Wako (manufactured by Wako Pure Chemical Industries).

(5) Result

In the mice administered the adenovirus having the inhibin βB gene, the blood glucose level immediately after glucose administration was significantly lower than control mice. While the control mice had a slight reduction in blood glucose level after 120 minutes from the glucose administration, the maximum blood glucose level after the glucose administration was reduced to a half or less in the mice administered the adenovirus having the inhibin βB gene. It has been indicated that insulin resistance can be improved by administering activin B, which is an FSTL3 binding protein (see FIG. 2-3).

3. Improvement in Insulin Resistance through Neutralizing Antibody (1) Administration of Antibody After six-week-old male db/db mice were adapted for one week, an anti-FSTL3 antibody or control antibody was intraperitoneally administered at 30 μg/body every other day, a total of five times. The following antibodies were used.

Anti-FSTL3 Antibody

Anti FLAG®, Mouse (Goat) (R&D SYSTEMS®)

Control Antibody

Goat IgG Control (R&D SYSTEMS®)

(2) Insulin Tolerance Test (ITT)

After administration of antibody, 3.0 mU/g-BW of insulin (diluted by physiological saline) was continuously administered into the abdominal cavities of mice without fasting. A glucose concentration was measured by Glutest Sensor (Sanwa Kagaku) from collected whole blood.

(3) Result

Figures 1, 2:
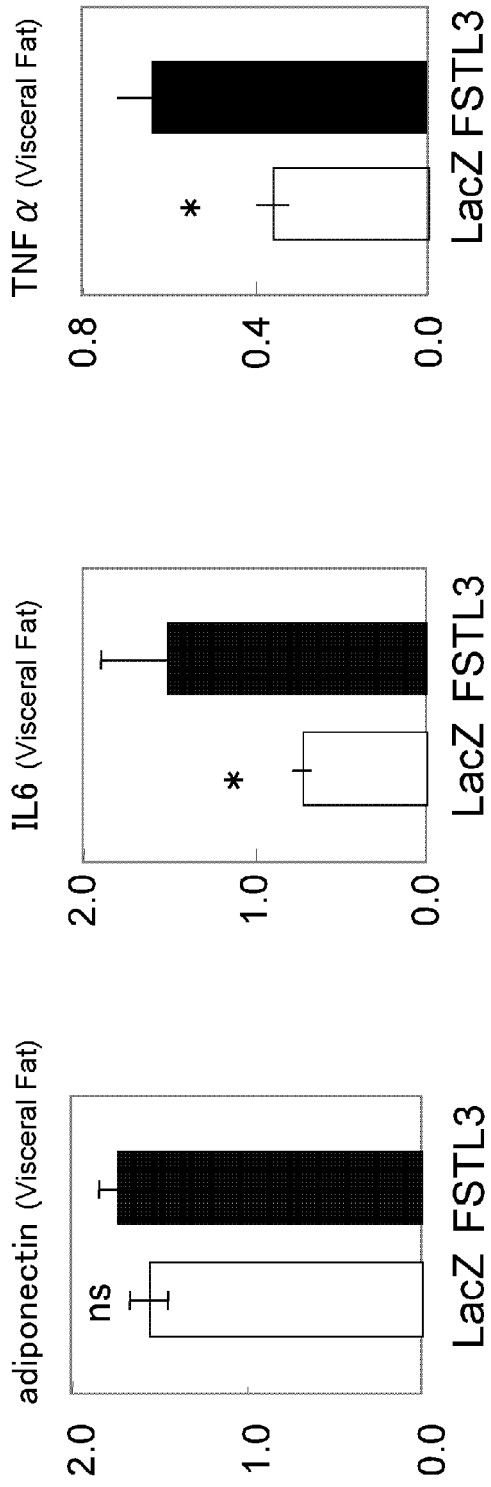
Figures 1, 2, 3:
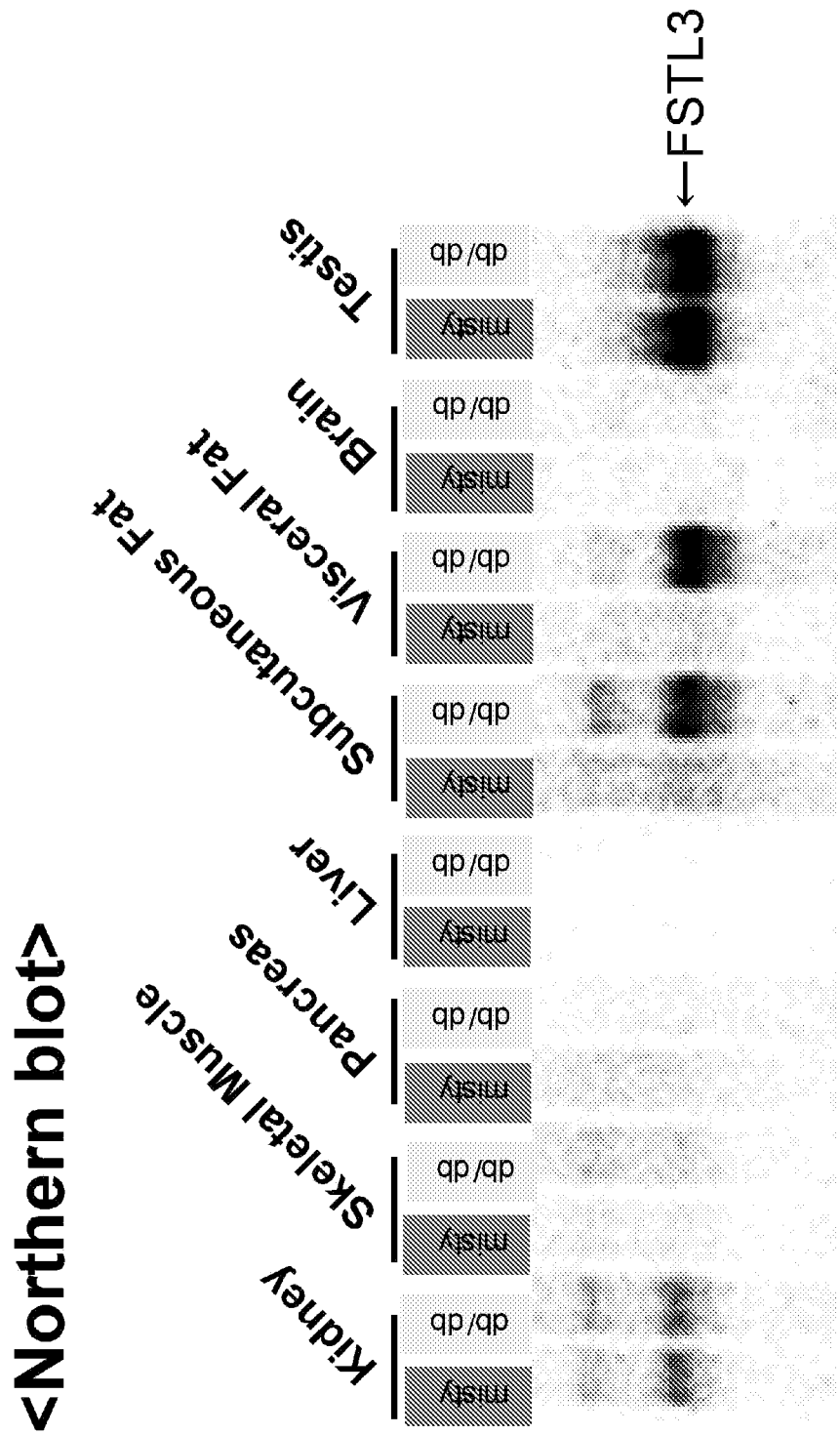
Figures 1, 2, 3, 4:
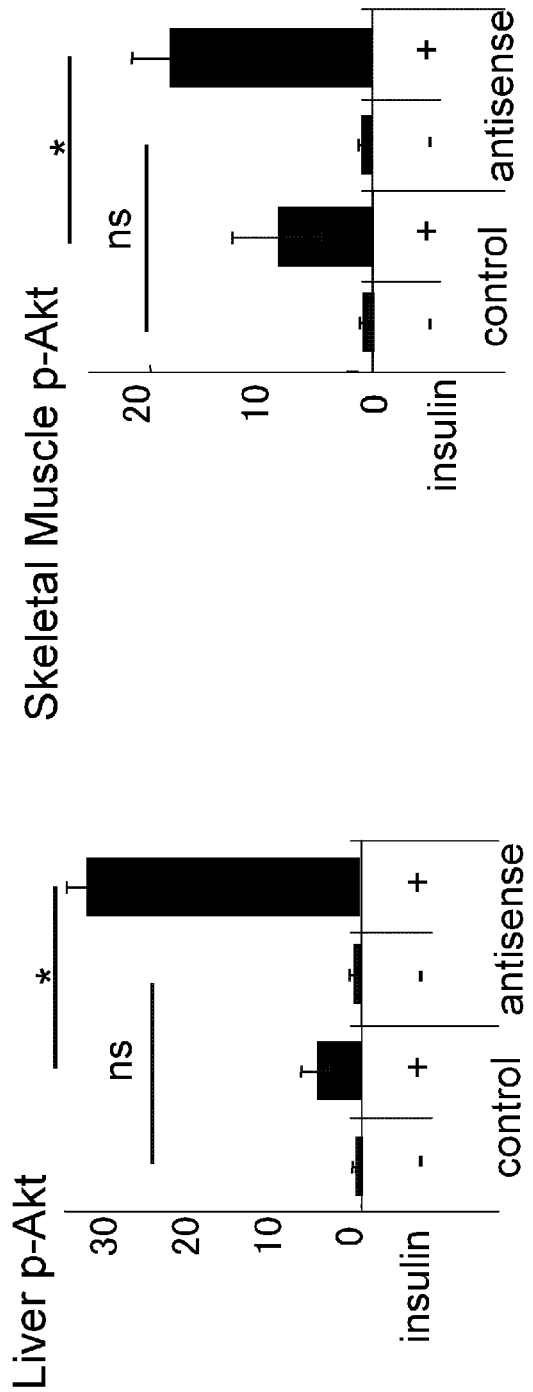
Figures 1, 2:
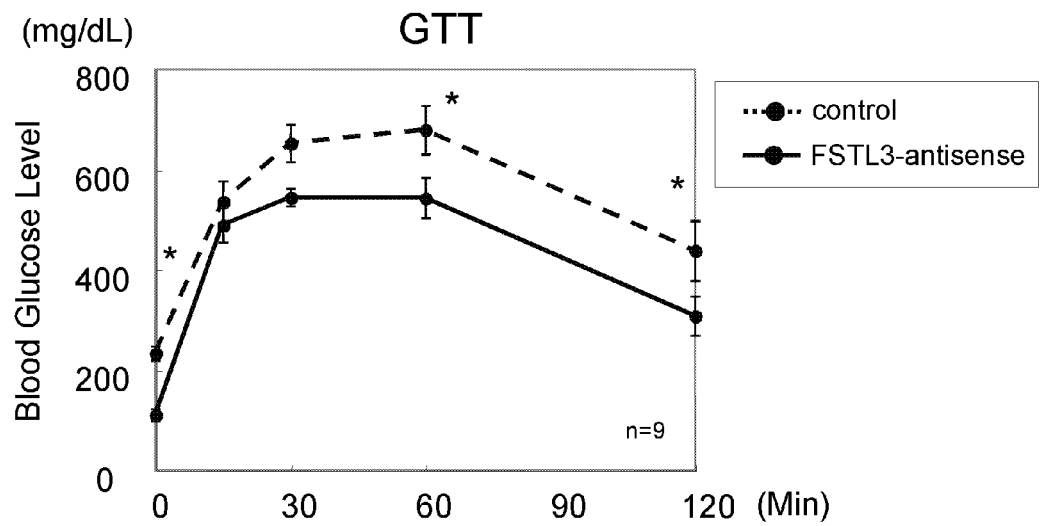
Figure 2:
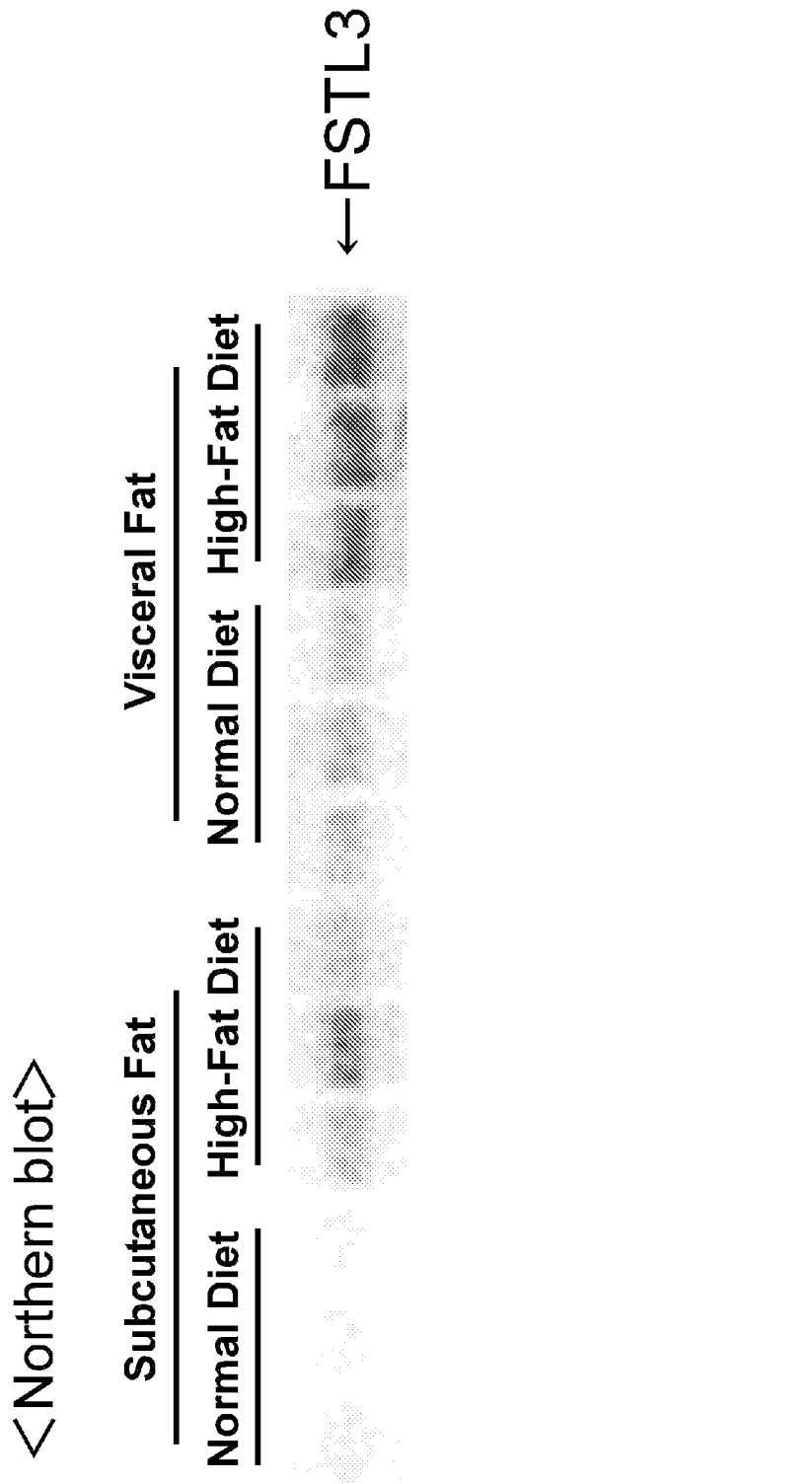
Figures 2, 3:
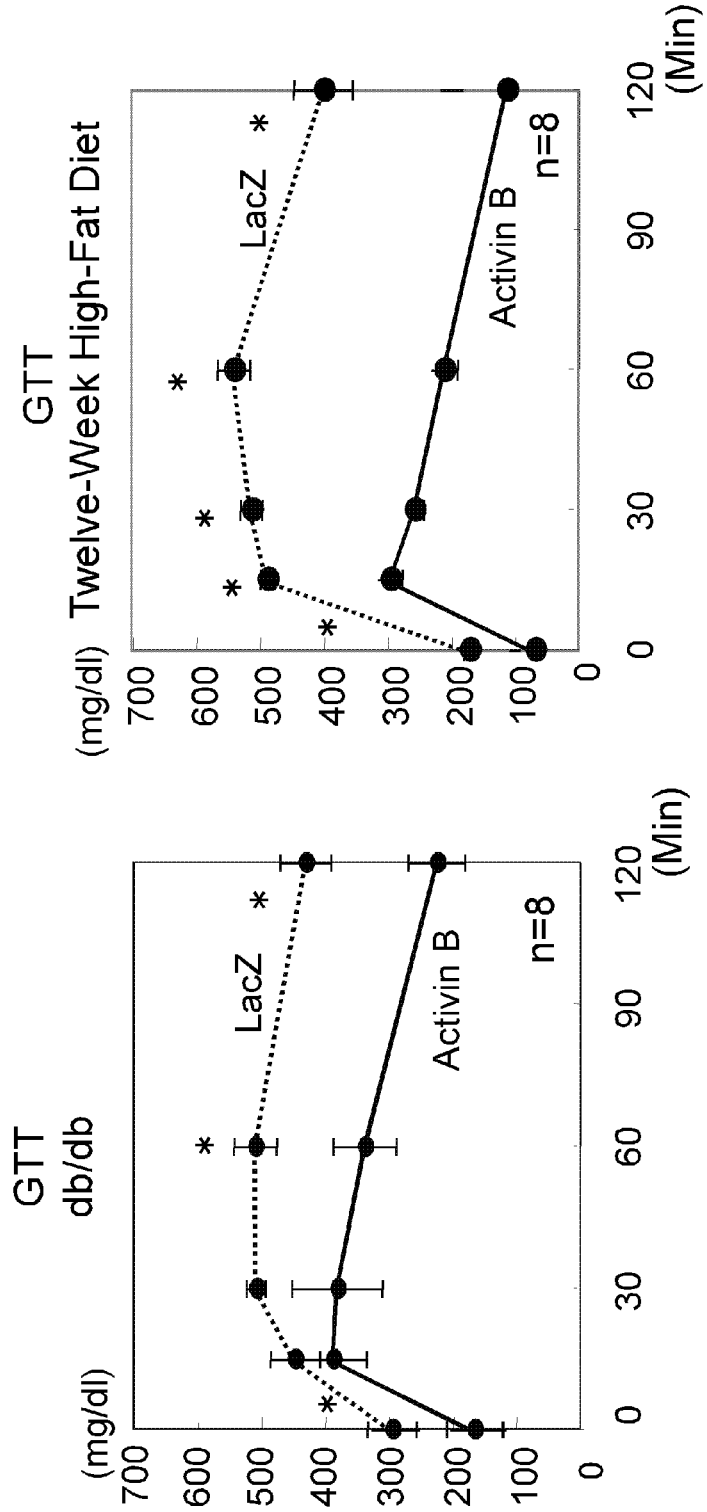
Figures 2, 3, 4:
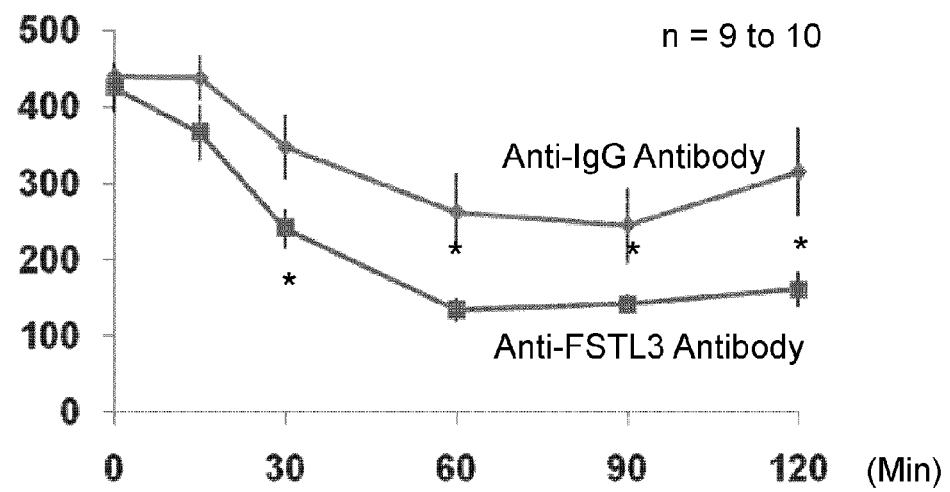

In the mice administered the anti-FSTL3 antibody, a blood glucose level was significantly reduced by insulin administration as compared to the control mice (see FIG. 2-4, the vertical axis and the horizontal axis indicate blood glucose level (mg/dL) and time (minute), respectively). It has been indicated that the administration of the anti-FSTL3 antibody can improve insulin resistance.

The invention claimed is:

1. A method for decreasing insulin resistance in a patient comprising: the step of administering to a patient with insulin resistance an effective amount of a Follistatin-like 3 (FSTL3) inhibitor, wherein the FSTL3 inhibitor is
one or more of activin B or activin AB.

2. The method of claim 1, wherein the administration of the inhibitor further comprises administering a pharmaceutically acceptable diluent or carrier with the one or more of activin B or activin AB.

3. A method for decreasing insulin resistance in a patient consisting of the step of:
   administering to a patient with insulin resistance, solely or in combination with another drug, an effective amount of a composition comprising Follistatin-like 3 (FSTL3) inhibitor, wherein the FSTL3 inhibitor is
   one or more of activin B or activin AB,
   and the composition further comprises one or more pharmaceutically acceptable diluents, carriers, additives, or excipients.

4. A method for decreasing insulin resistance in a patient comprising the step of:
   administering to a patient with insulin resistance a pharmaceutical composition consisting of:
   an effective amount of a Follistatin-like 3 (FSTL3) inhibitor, wherein the FSTL3 inhibitor is
   one or more of activin A, activin B or activin AB, and
   one or more pharmaceutically acceptable diluents, carriers, additives, or excipients.

* * * * *